(12) United States Patent
Zhang et al.

(10) Patent No.: US 6,879,754 B2
(45) Date of Patent: Apr. 12, 2005

(54) DROP-BEFORE-ADD OPTICAL SWITCHING AND ROUTING SYSTEM EMPLOYING GRATING-BASED WAVELENGTH SELECTIVE SWITCHES

(75) Inventors: Jianjun Zhang, Cupertino, CA (US); Peiching Ling, San Jose, CA (US); Jinliang Chen, Saratoga, CA (US); Ming Xu, San Jose, CA (US)

(73) Assignee: Integrated Optics Communications Corporation, Sunnyvale, CA (US)

( * ) Notice: Subject to any disclaimer, the term of this patent is extended or adjusted under 35 U.S.C. 154(b) by 123 days.

(21) Appl. No.: 10/188,955

(22) Filed: Jul. 3, 2002

(65) Prior Publication Data

US 2003/0108289 A1 Jun. 12, 2003

Related U.S. Application Data

(60) Provisional application No. 60/338,927, filed on Dec. 10, 2001, provisional application No. 60/346,066, filed on Jan. 3, 2002, provisional application No. 60/346,567, filed on Jan. 8, 2002, and provisional application No. 60/373,803, filed on Apr. 19, 2002.

(51) Int. Cl.$^7$ ................................................ G02B 6/34
(52) U.S. Cl. .............................. 385/37; 385/37; 385/10; 385/16; 385/17; 385/24; 372/102
(58) Field of Search ....................... 385/37, 10, 16–17, 385/24; 372/102

(56) References Cited

U.S. PATENT DOCUMENTS

| | | | | |
|---|---|---|---|---|
| 5,255,332 A | * | 10/1993 | Welch et al. ................. | 385/17 |
| 5,488,681 A | * | 1/1996 | Deacon et al. ................. | 385/37 |
| 5,581,643 A | * | 12/1996 | Wu .............................. | 385/17 |
| 5,652,817 A | * | 7/1997 | Brinkman et al. ............. | 385/37 |
| 5,778,119 A | | 7/1998 | Farries | |
| 5,875,272 A | | 2/1999 | Kewitsch et al. | |
| 6,061,484 A | | 5/2000 | Jones et al. | |
| 6,289,699 B1 | | 9/2001 | Kewitsch et al. | |
| 6,360,038 B1 | | 3/2002 | Grubsky | |
| 6,522,795 B1 | | 2/2003 | Jordan et al. | |
| 6,567,573 B1 | | 5/2003 | Domash et al. | |
| 6,606,427 B1 | * | 8/2003 | Graves et al. ................. | 385/17 |
| 6,650,807 B2 | * | 11/2003 | Wang ........................... | 385/22 |
| 2001/0046352 A1 | | 11/2001 | Ohta et al. | |
| 2002/0150330 A1 | | 10/2002 | Kopp et al. | |
| 2002/0181855 A1 | * | 12/2002 | Xue et al. ..................... | 385/23 |

* cited by examiner

Primary Examiner—Thien M. Lee
Assistant Examiner—Edwyn Labaze
(74) Attorney, Agent, or Firm—Perkins Coie LLP

(57) ABSTRACT

The present invention discloses a drop-before-add optical routing and switching system. The drop-before-add optical routing and switching system includes an input waveguide for carrying a multiplexed optical signal comprising optical signals transmitted over a plurality of wavelength channels represented by $\lambda_1, \lambda_2, \lambda_3, \ldots, \lambda_{N-1}$ and $\lambda_N$, where N is a positive integer wherein the input waveguide extending over a first direction. The drop-before-add optical routing and switching system further includes a plurality of second direction waveguides extending over a second direction and intersecting at N intersections with the input waveguide. The drop-before-add optical routing and switching system further includes a plurality of wavelength selective grating switches each disposed on one of the N intersections for selectively transmitting an optical signal of a selected wavelength into an associated one of the second direction waveguide.

19 Claims, 16 Drawing Sheets

DROP-BEFORE-ADD OPTICAL SWITCHING AND ROUTING SYSTEM EMPLOYING GRATING-BASED WAVELENGTH SELECTIVE SWITCHES

Priority is hereby claimed under 35 U.S.C. § 120 to U.S. Provisional Patent Application Ser. No. 60/338,927 filed Dec. 10, 2001, U.S. Provisional Patent Application Ser. No. 60/346,066 filed Jan. 3, 2002, U.S. Provisional Patent Application No. 60/346,567 filed Jan. 8, 2002, U.S. Provisional Patent Application Ser. No. 60/373,803, filed Apr. 19, 2002, U.S. patent application No. 10/104,273 filed Mar. 22, 2002, and U.S. patent application Ser. No. 10/177,632 filed Jun. 19, 2002, each of which is incorporated by reference.

BACKGROUND OF THE INVENTION

1. Field of the Invention

This invention relates generally to technologies for switching and routing optical wavelengths, and more particularly, this invention relates to waveguide grating-based wavelength selective switches and to add/drop devices comprising these wavelength selective switches.

2. Description of the Related Art

Optical wavelength division multiplexing (WDM) is a very important method used in modern optical fiber communication systems to dramatically increase the data transmission rate. In WDM systems, the whole optical beam consists of a number of different wavelength optical signals (wavelength channels). Each wavelength channel carries its own data information transmitted over the fiber. Therefore, with WDM technology a single optical fiber can transmit a number of distinguishable optical signals simultaneously. The result is a significant increase of effective bandwidth of the optical fiber and data transmission rate of the communication system.

In the WDM networks of the past, adding, dropping or cross connecting of individual wavelengths has involved conversion of the optical signal back to the electrical domain. Development of all-optical switches for applications ranging from add-drop functionality to large-scale cross-connects is key to adding intelligence to the optical layer of the optical networking systems. However, with the current technical limitations, all fiber network systems implemented with optical switches are still quite expensive.

To employ WDM technology in an optical communication system, optical demultiplexers, switches, multiplexers, and add/drop devices are important. Current state of the art in optical switching and signal transmission systems are limited to optical switching of an entire spectral range without wavelength differentiation or selection. Due to the lack of wavelength selection, an optical switch operation must frequently operate with a wavelength de-multiplexing and multiplexing device to achieve the transfer of optical signals of different wavelengths to different ports. This requirement leads to more complicated system configurations, higher manufacture and maintenance costs, and lower system reliability. For this reason, even though optical switches provide an advantage that the optical signals are switched entirely in the optical domain without converting them into the electrical domain, the cost and size of system cannot be easily reduced.

An add/drop device is used to inject (add) or extract (drop) one or more wavelength channels to or from a WDM network. Current optical add/drop devices usually consist of various types of optical switches and require optical multiplexers and demultiplexers, as shown in FIGS. 1A and 1B. FIG. 1A shows a typical block diagram of an optical add/drop device. Through the optical add/drop device, wavelength channels can be added or dropped to or from the main optical transmission trunk. FIG. 1B illustrates the construction of a typical prior-art optical add/drop device. This optical add/drop device requires a demultiplexer and a multiplexer to carry out wavelength selective switching operations in order to accomplish the add/drop functions. The requirement of a demultiplexer and a multiplexer makes the prior-art optical add/drop devices complex and costly to build. For a simple add/drop matrix, this requirement of a demultiplexer and a multiplexer is a significant burden. In addition, for a larger add/drop matrix, these prior-art optical add/drop devices suffer from their rapidly increasing complexity as the matrix size grows.

Due to the requirement of optical multiplexers and demultiplexers as well as functionality limitation of these optical switches, optical add/drop devices built upon these optical switches usually suffer from complexity, inflexibility, and high cost.

BRIEF DESCRIPTIONS OF THE DRAWINGS

The present invention can be better understood with reference to the following drawings. The components within the drawings are not necessarily to scale relative to each other, emphasis instead being placed upon clearly illustrating the principles of the present invention.

Figure 3A:
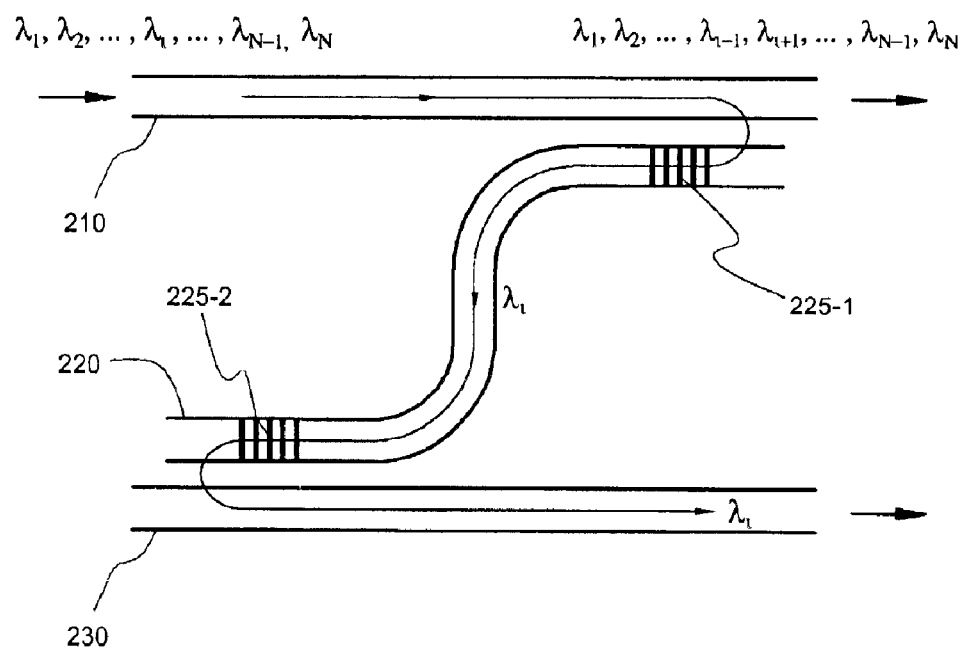
Figure 3B:
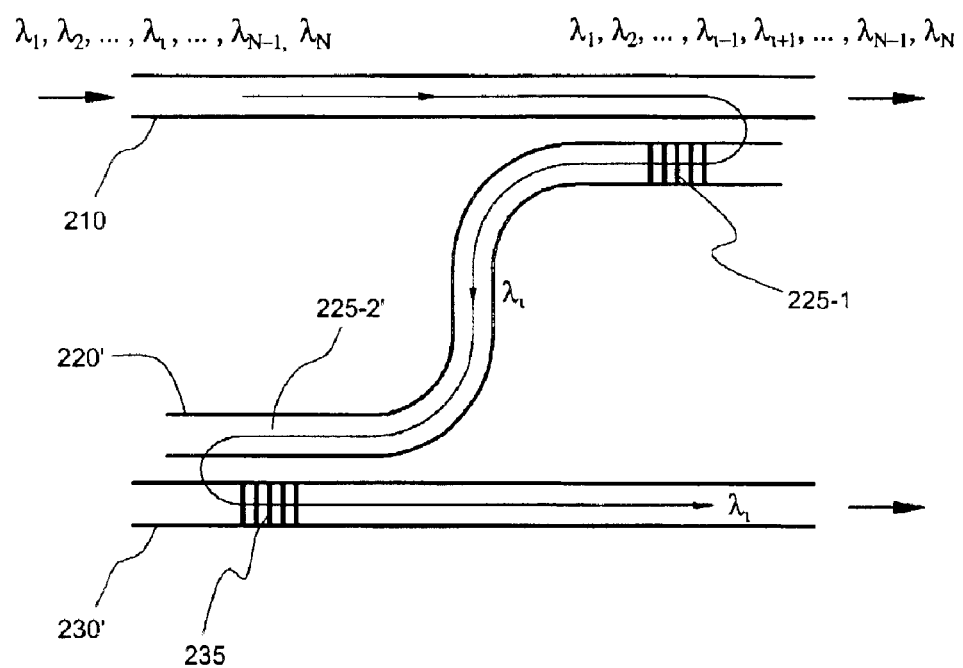
Figure 3C:
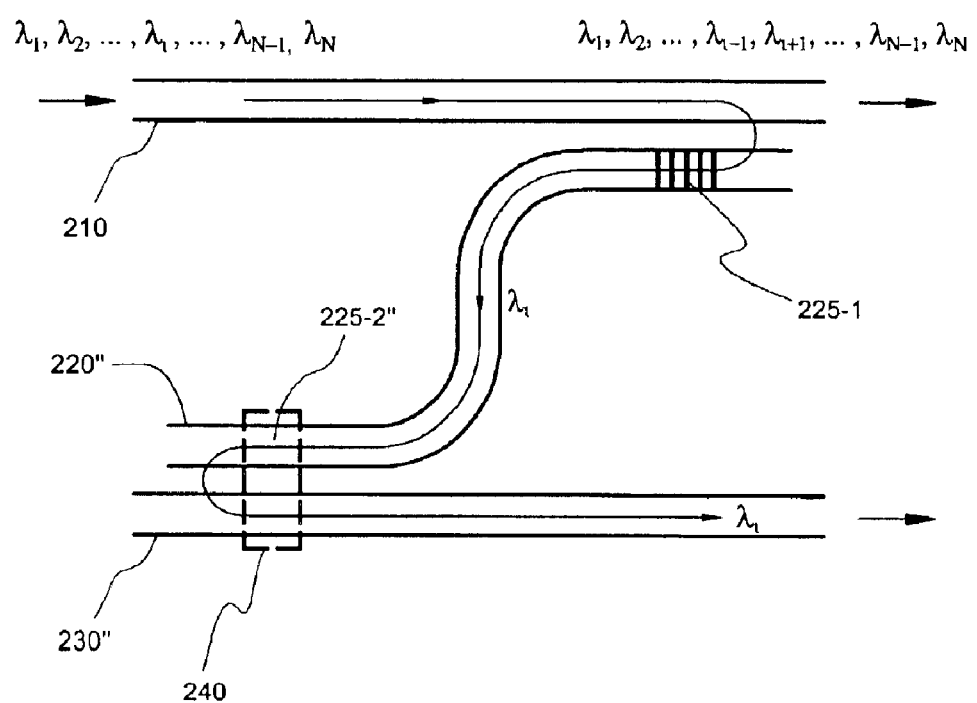

FIGS. 3A, 3B, and 3C are cross sectional views for showing the coupling configurations of a wavelength-selective bridge waveguide coupled between a bus waveguide and an outbound waveguide.

Figure 4A:
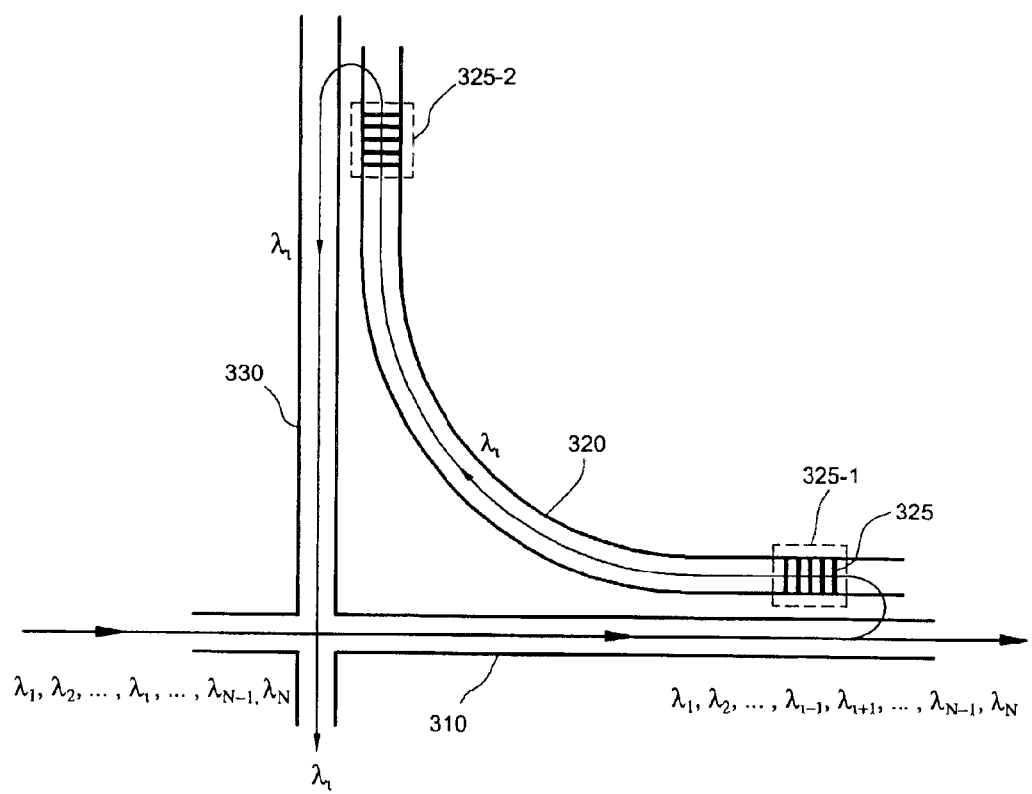
Figure 4B:
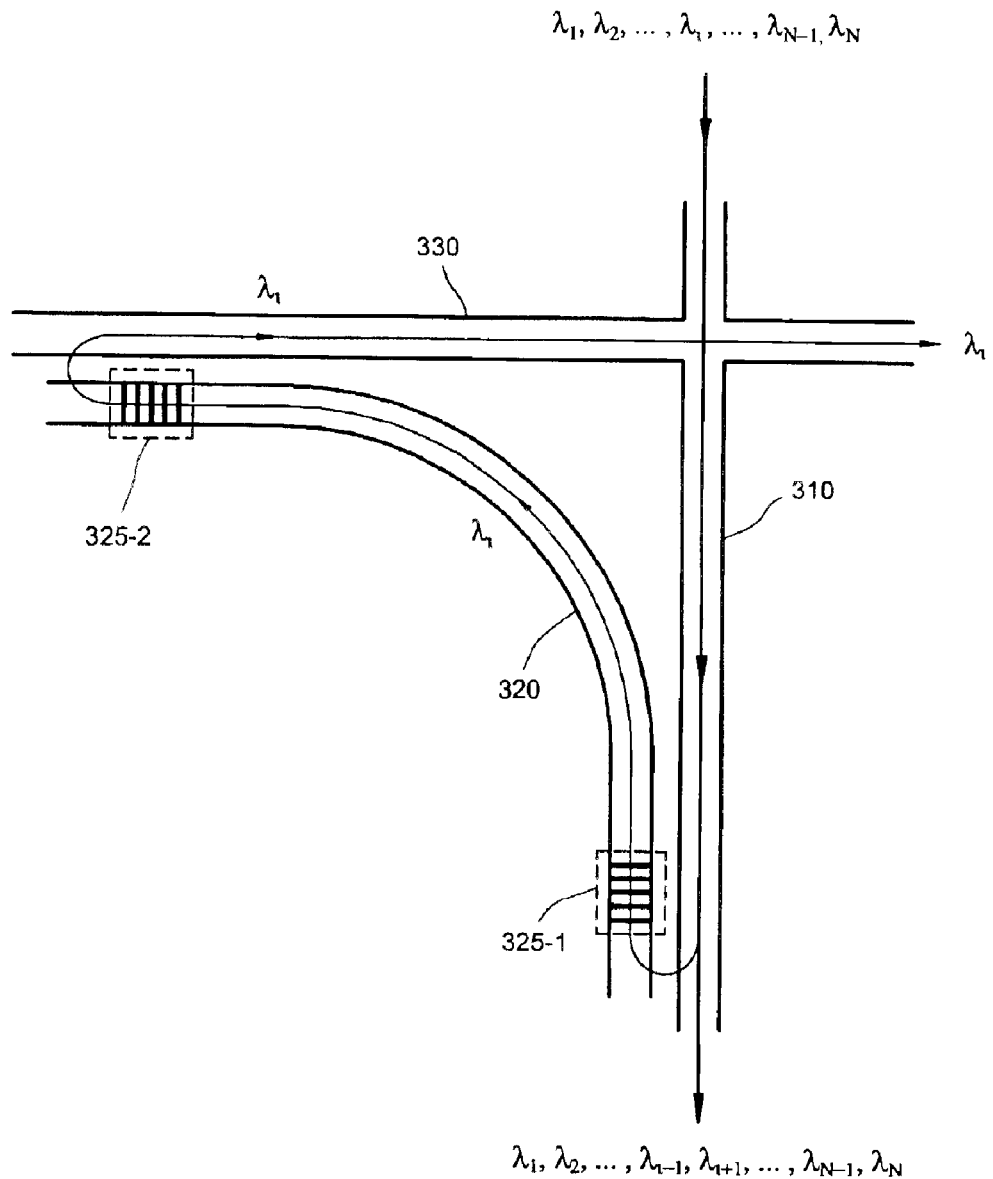

FIGS. 4A and 4B are functional diagrams for showing wavelength selective bridge waveguide coupled between the intersecting waveguides for switching and re-directing optical transmission of a selected wavelength.

Figure 5:
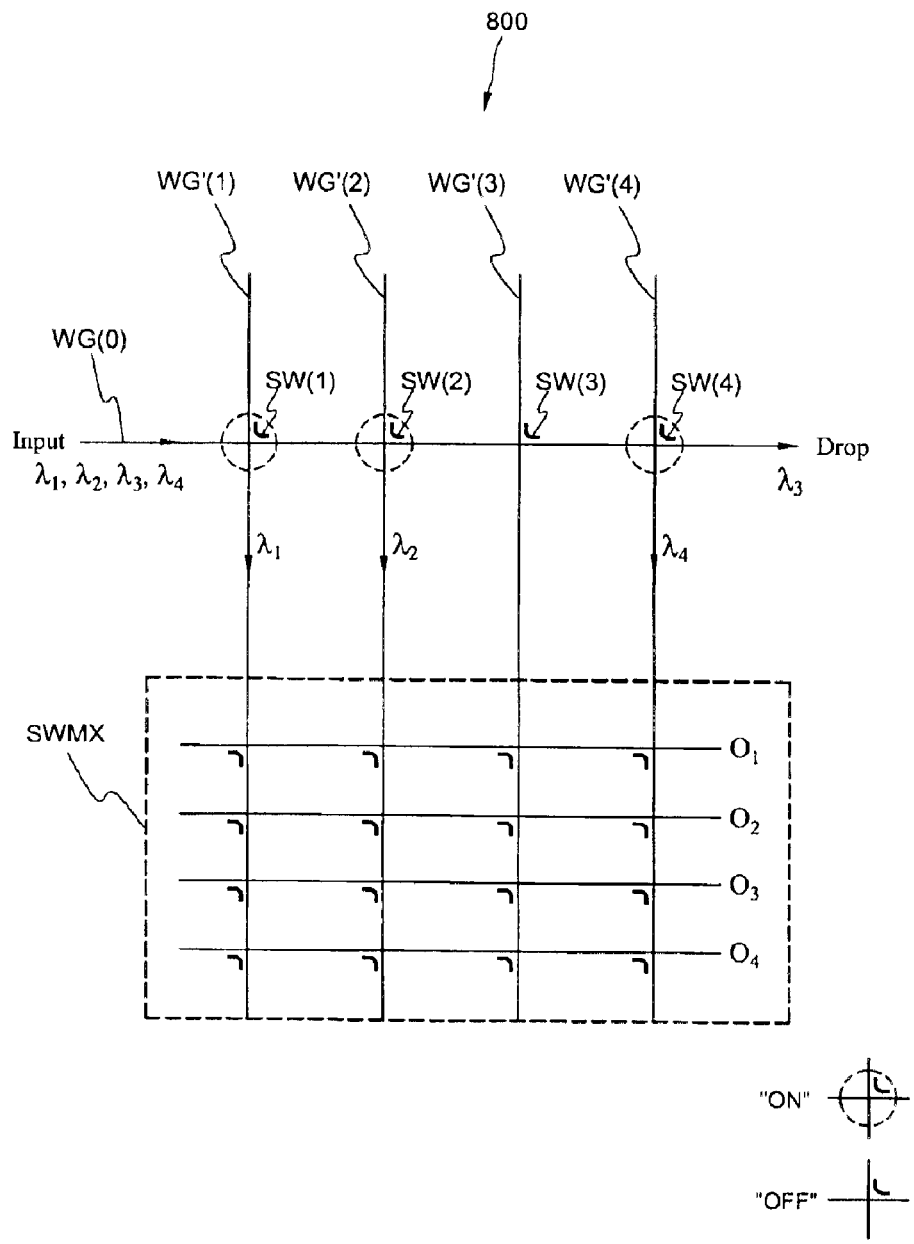

FIG. 5 is a drop-before-add signal routing and switching system wherein a multiple-channel input optical signal is inputted into an input waveguide and signals of drop channels are selected and transmitted via the input waveguide without using a de-multiplexing device.

Figure 6:
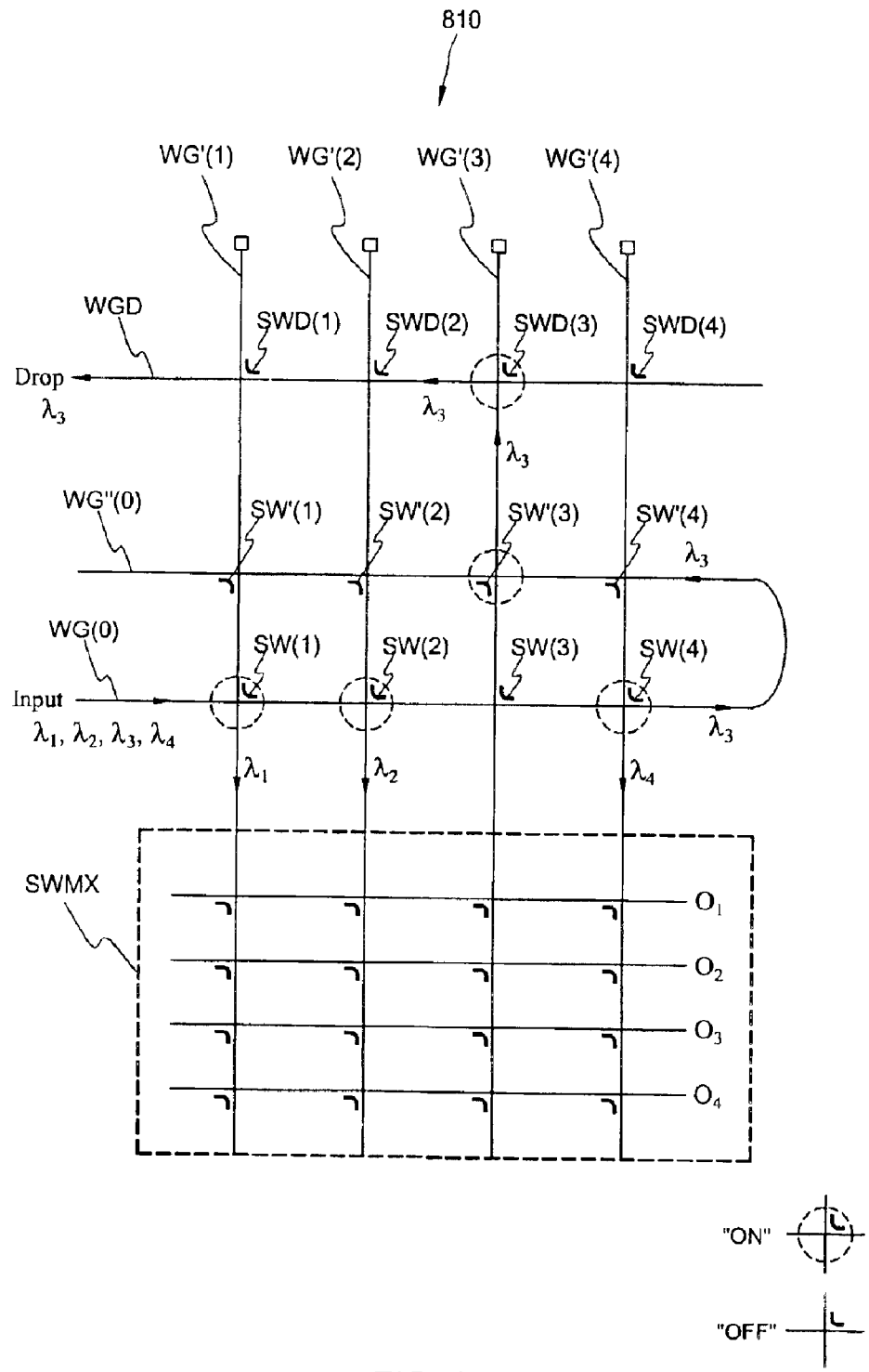

FIG. 6 is a drop-before-add signal routing and switching system similar to that of FIG. 5 with an input extension for drop-signal transmission and an additional drop waveguide to monitor the drop and residual signals.

Figure 7:
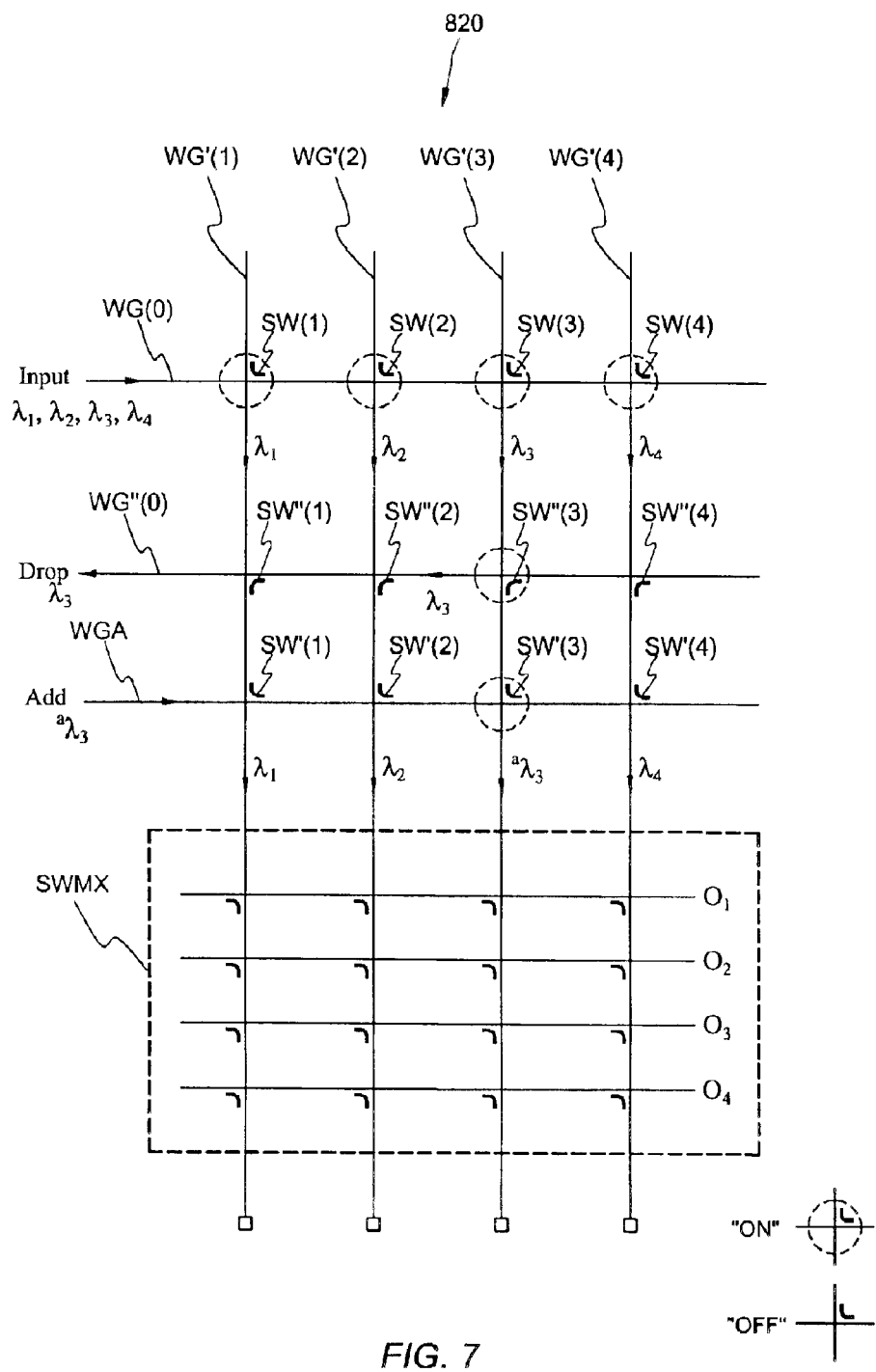

FIG. 7 is a drop-before-add signal routing and switching system similar to that of FIG. 5 with an input, add and drop waveguides for first transmitting the drop-signals via the drop waveguide before the add-signals are added.

Figure 8:
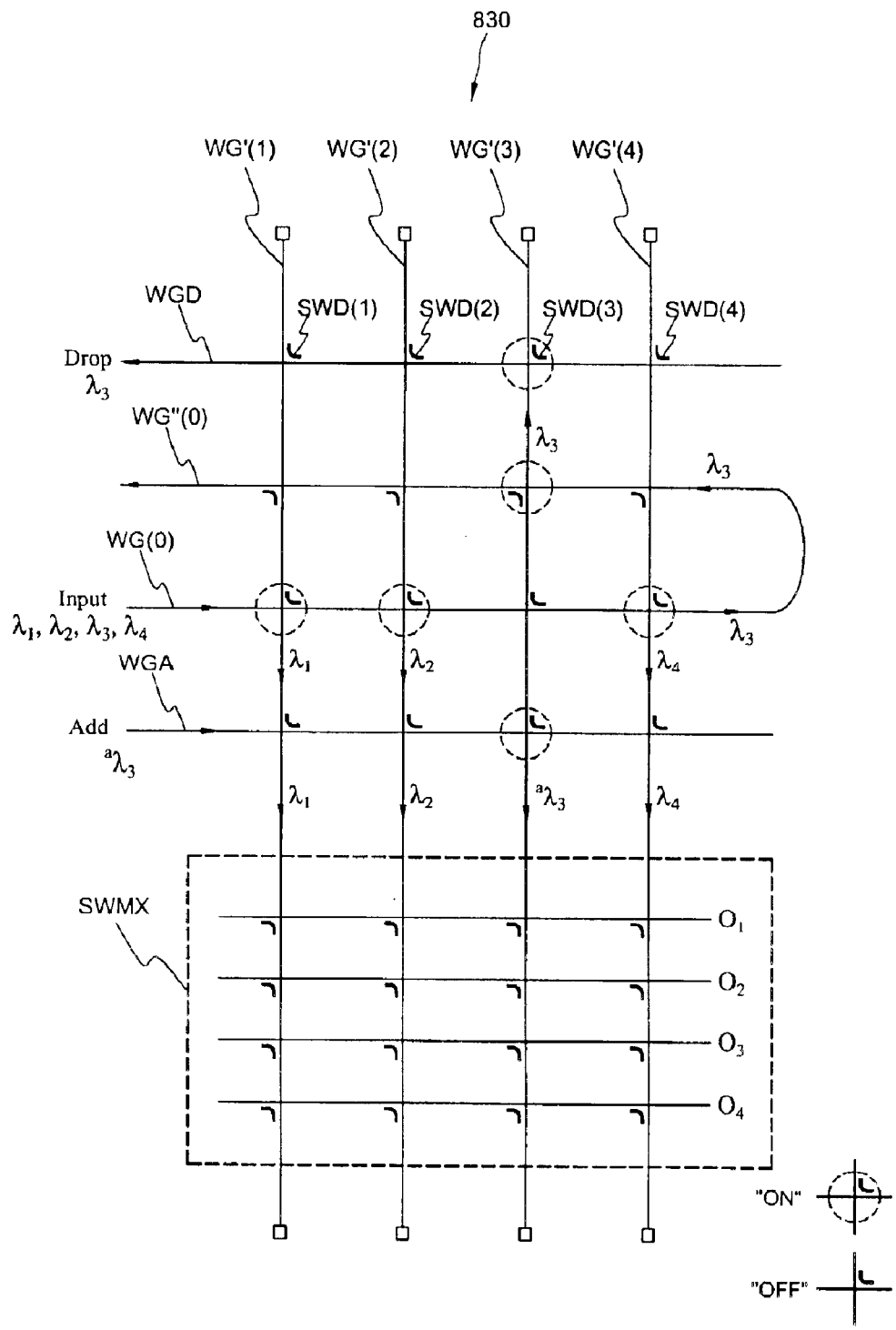

FIG. 8 is a drop-before-add signal routing and switching system similar to that of FIG. 6 with an additional waveguide for inputting add signals.

Figure 9:
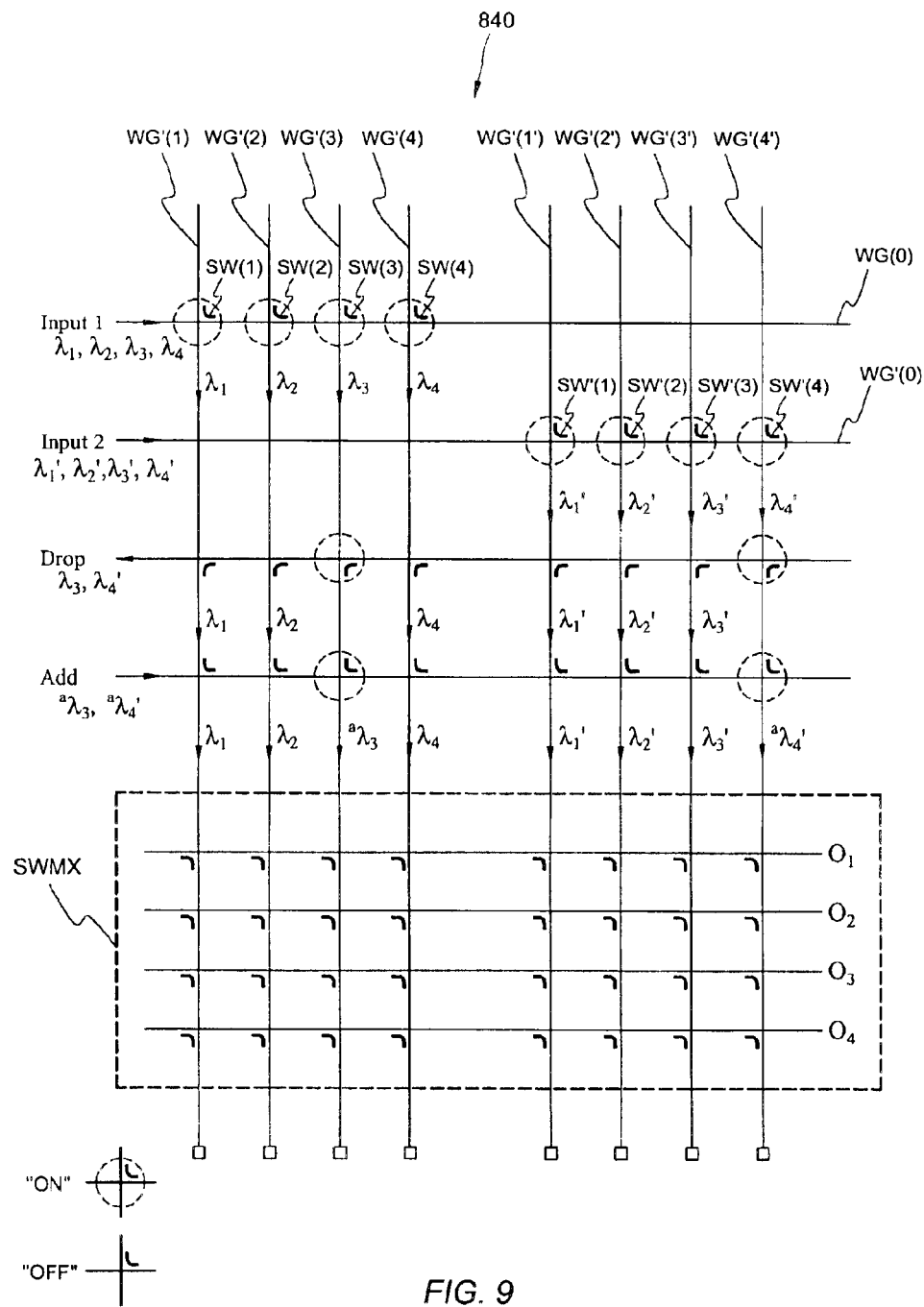

FIG. 9 is a drop-before-add signal routing and switching system similar to that of FIG. 7 with two input waveguides for inputting two input signals with two sets of multiple wavelength channels.

Figure 10:
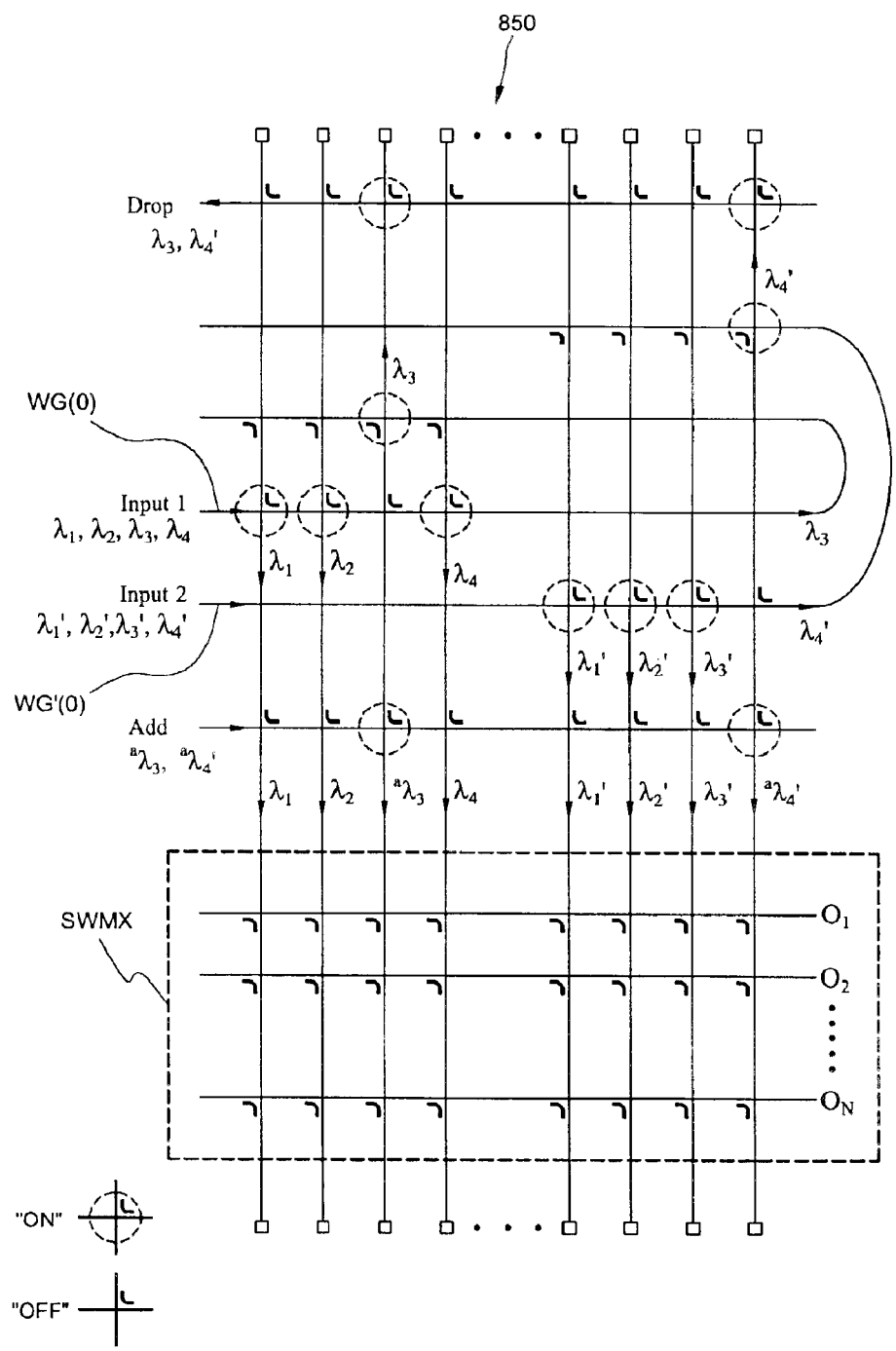

FIG. 10 is a drop-before-add signal routing and switching system similar to that of FIG. 9 with two input waveguide extensions for dropping signals from these two extension waveguides.

Figure 11:
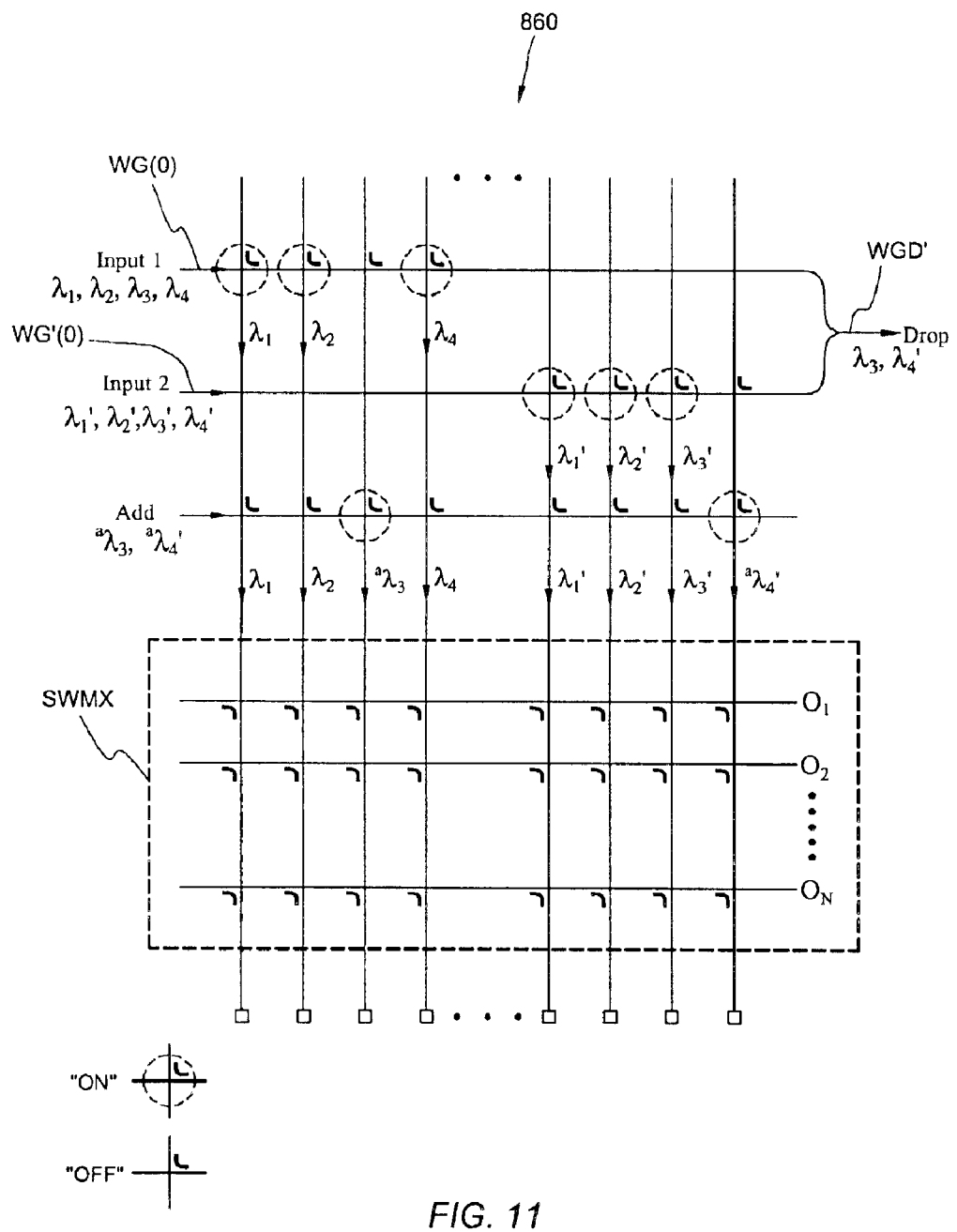

FIG. 11 is a drop-before-add signal routing and switching system similar to that of FIG. 9 with two input waveguides for inputting two input signals with two sets of multiple wavelength channels and then merged into a drop output waveguide.

Figure 12:
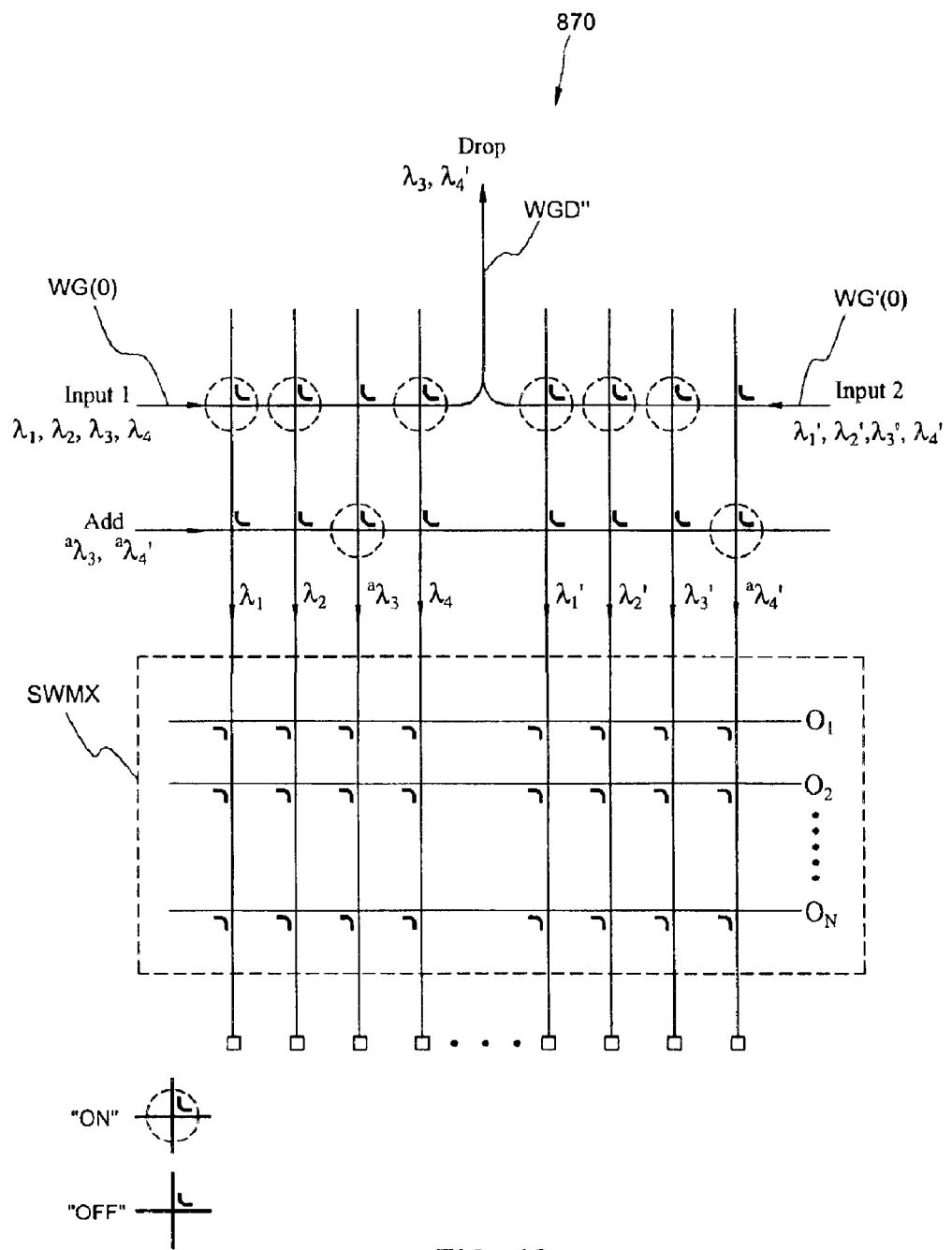

FIG. 12 is a drop-before-add signal routing and switching system configured as a variation from that shown in FIG. 10 with two input waveguides for inputting two input signals with two sets of multiple wavelength channels and then merged into a drop output waveguide.

DETAILED DESCRIPTION OF THE PREFERRED EMBODIMENT

The present invention utilizes MEMS-actuated waveguide grating-based wavelength intelligent switches, as disclosed in our co-pending applications noted above. The switch is fabricated on a silicon substrate and the switching action is based on electrostatic bending of a part of waveguide with integrated Bragg gratings built in its cladding layer. The waveguide with integrated Bragg gratings, defined as a "bridge waveguide", functions as a switching element. When the bridge waveguide is electrostatically bent close enough to an input waveguide, the wavelength which meets the Bragg phase-matching condition is coupled into the bridge waveguide. Through the bridge waveguide, the selected wavelength is then directed into a desired output waveguide.

Electrostatic bending of a waveguide with integrated Bragg grating can be implemented by simply applying a voltage between a silicon substrate and an electrode. This can greatly simplify the production of large-scale optical switches, compared with the prior art micro-mirror based MEMS approach. The integrated Bragg grating is formed by physically corrugating a waveguide. Thus, it does not reply upon a photorefractive index change, which enables building Bragg gratings in material that are not photorefractive and enhancing the grating strength. The integrated Bragg grating can be made smaller, and packed closer together than fiber-optic device. This opens the door for leveraging IC processing to fabricate the highly integrated optical switches.

Figure 1A:
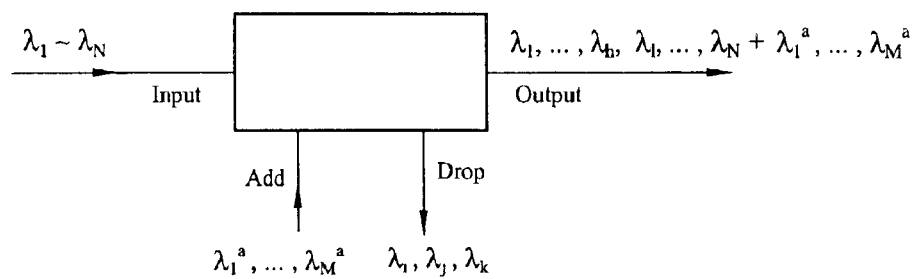
FIG. 1A shows a block diagram of a prior art optical add/drop device.
Figure 1B:
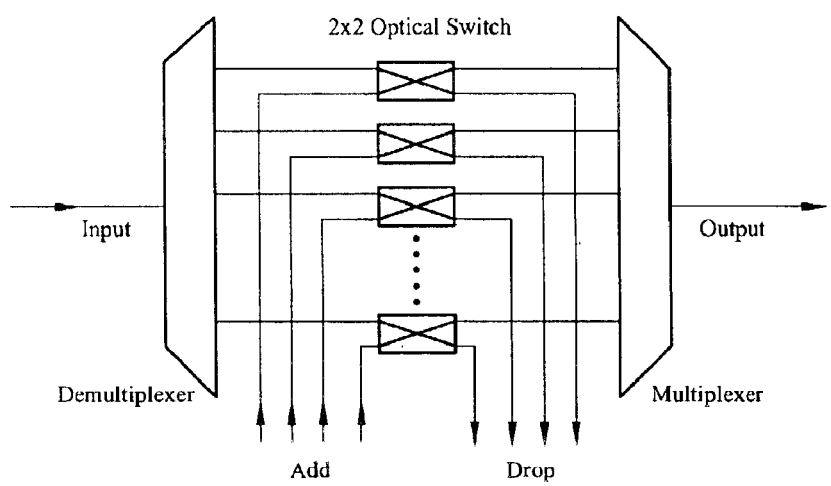
FIG. 1B illustrates the construction of a prior-art optical add/drop device.
Figure 2A:
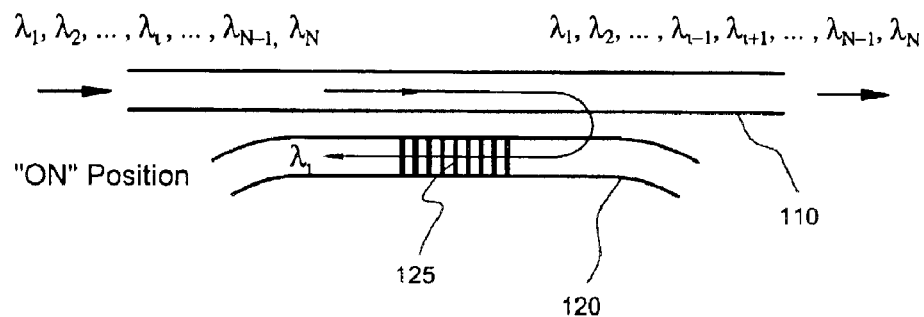
FIGS. 2A and 2B are schematic diagrams showing the on/off switching functions of a Bragg grating wavelength selective bridge waveguide.
Figure 2B:
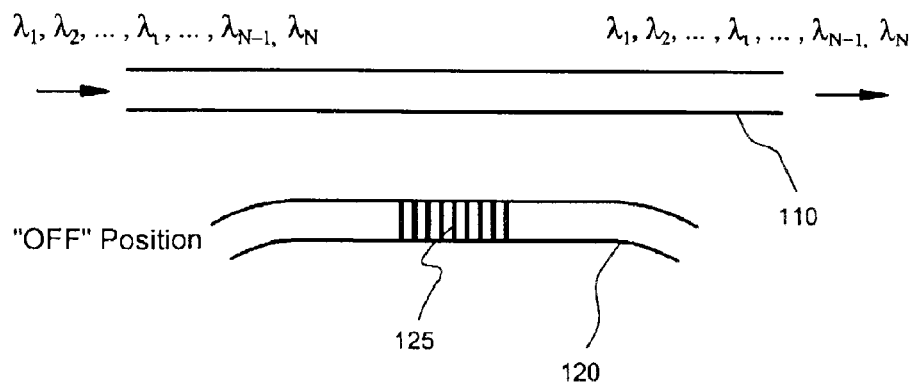

FIGS. 2A and 2B are schematic diagrams showing the on and off states respectively of a wavelength-selective bridge waveguide 120 relative to a multi-channel bus waveguide 110. A multiplexed optical signal is transmitted in a bus waveguide 110 over N multiplexed wavelengths $\lambda_1$, $\lambda_2$, $\lambda_3$, ..., $\lambda_N$, where N is a positive integer. In FIG. 2A, the wavelength selective bridge waveguide 120 is moved to an on-position and coupled to the waveguide 110. An optical signal with a central wavelength $\lambda i$ particular to the Bragg gratings 125 disposed on the bridge waveguide 120 is guided into the wavelength selective bridge waveguide 120. The remainder optical signal of the wavelengths $\lambda_1, \lambda_2, \ldots, \lambda_{i-1}, \lambda_{i+1}, \ldots, \lambda_N$ is not affected and continues to transmit over the waveguide 110. The Bragg gratings 125 have a specific pitch for reflecting the optical signal of the selected wavelength $\lambda_i$ onto the wavelength selective bridge waveguide 120. In FIG. 2B, the wavelength selective bridge waveguide is pulled off from the waveguide 110 to a "bridge-off" position. There is no "detoured signal" entering into the bridge waveguide. The entire multiplexed signal over wavelengths $\lambda_1, \lambda_2, \lambda_3, \ldots, \lambda_N$ continue to transmit on the bus waveguide 110.

Figure 2C:
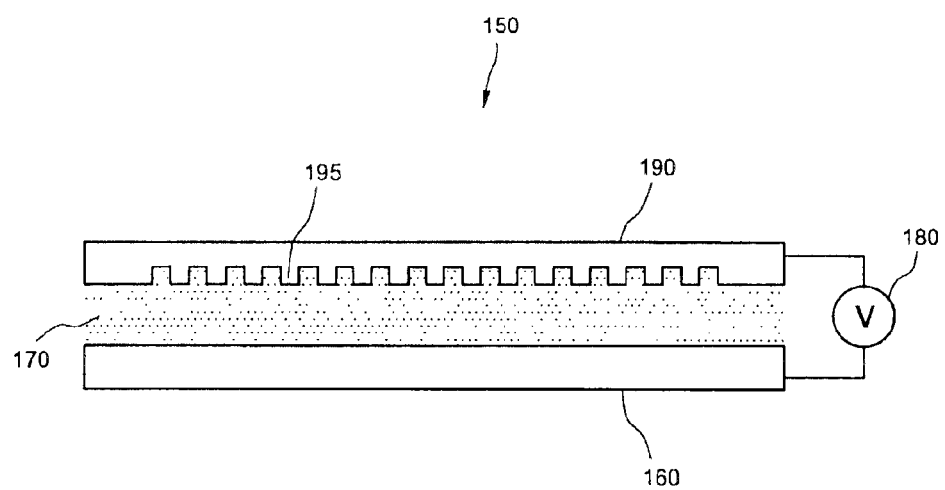
FIG. 2C is a Bragg grating switch implemented with a cavity filled with a medium with a variable refraction index for turning on and off the Bragg grating switching function by adjusting the refractive index of the medium.

Referring to FIG. 2C for a wavelength selective Bragg grating based switching device 150. The wavelength selective switching device 150 is formed with two adjacent waveguides 190 and 160. These two waveguides 190 and 160 can be either vertically or horizontally arranged as side by side waveguides where waveguide 190 is formed with Bragg gratings with specific wavelength selective characteristic for wavelength selective reflection or transmission. Between these two waveguides 190 and 160, a space is filled with a refraction index variable medium 170. The refraction index of the medium 170 is changed when a voltage is applied by a voltage input, e.g., a DC power supply 180. When the voltage input is turned on, there is an index mismatch and there exists a grating effect for performing a wavelength selective reflection or transmission function. When the voltage input 180 is turned off, the refraction index is changed to match with that of the Bragg gratings 195 and the grating effects disappear. Therefore, by turning on or off the DC voltage power supply, the wavelength selective switch 150 can be alternately turned off or on. The refraction-index-matching medium may be a refraction index matching liquid crystal filling in the space between two optical waveguides.

FIG. 3A shows structure of an "S" type switch. A wavelength selective bridge waveguide 220 is coupled between a bus waveguide 210 and a second waveguide 230. A multiplexed optical signal is transmitted in a bus waveguide 210 over N multiplexed wavelengths $\lambda_1, \lambda_2, \lambda_3, \ldots, \lambda_N$, where N is a positive integer. The wavelength selective bridge waveguide 220 has a first set of Bragg gratings disposed on a first "bridge on-ramp segment" 225-1 for coupling to the bus waveguide 210. An optical signal with a central wavelength $\lambda_i$ particular to the Bragg gratings 225 disposed on the bridge waveguide 220 is guided through the first bridge ramp segment 225-1 to be reflected into the wavelength selective bridge waveguide 220. The remainder optical signal of the wavelengths $\lambda_1, \lambda_2, \ldots, \lambda_{i-1}, \lambda_{i+1}, \ldots, \lambda_N$ is not affected and continues to transmit over the waveguide 210. The Bragg gratings 225 have a specific pitch for reflecting the optical signal of the selected wavelength $\lambda_i$ onto the wavelength selective bridge waveguide 220. The wavelength selective bridge waveguide 220 further has a second set of Bragg gratings as a bridge off-ramp segment 225-2 coupled to an outbound waveguide 230. The second set of Bragg gratings has a same pitch as the first set of Bragg gratings. The selected wavelength $\lambda_i$ is guided through the bridge off-ramp segment 225-2 to be reflected and coupled into the outbound waveguide 230. The bridge off-ramp segment 225-2 is disposed at a distance from the bridge on-ramp segment 225-1. The bridge waveguide 220 can be an optical fiber, waveguide or other optical transmission medium connected between the bridge on-ramp segment 225-1 and the bridge off-ramp segment 225-2.

FIG. 3B shows another structure of "S" type switches. A wavelength selective bridge waveguide 220' is coupled between a bus waveguide 210 and a second waveguide 230'. A multiplexed optical signal is transmitted in a bus waveguide 210 over N multiplexed wavelengths $\lambda_1, \lambda_2, \lambda_3, \ldots, \lambda_N$, where N is a positive integer. The wavelength selective bridge waveguide 220' has a first set of Bragg gratings disposed on a first "bridge on-ramp segment" 225-1 for coupling to the bus waveguide 210. An optical signal with a central wavelength $\lambda_i$ particular to the Bragg gratings 225-1 disposed on the bridge waveguide 220' is guided through the first bridge ramp segment 225-1 to be reflected into the wavelength selective bridge waveguide 220'. The remainder optical signal of the wavelengths $\lambda_1, \lambda_2, \ldots,$ $\lambda_{i-1}, \lambda_{i+1}, \ldots, \lambda_N$ is not affected and continues to transmit over the waveguide 210. The Bragg gratings 225-1 have a specific pitch for reflecting the optical signal of the selected wavelength $\lambda_i$ into the wavelength selective bridge waveguide 220'. The wavelength selective bridge waveguide 220' further has a bridge off-ramp segment 225-2' coupled to an outbound waveguide 230' near a section 235 of the outbound waveguide 230. The section 235 on the outbound waveguide 230' has a second set of Bragg gratings having a same pitch as the first set of Bragg gratings. The bridge off-ramp segment 225-2' is disposed at a distance from the bridge on-ramp segment 225-1. The bridge waveguide 220 can be an optical fiber, waveguide or other optical transmission medium connected between the bridge on-ramp segment 225-1 and the bridge off-ramp segment 225-2'.

FIG. 3C shows another structure of "S" type switches. A wavelength selective bridge waveguide 220" is coupled between a bus waveguide 210 and a second waveguide 230". A multiplexed optical signal is transmitted in a bus waveguide 210 over N multiplexed wavelengths $\lambda_1, \lambda_2, \lambda_3, \ldots, \lambda_N$ where N is a positive integer. The wavelength selective bridge waveguide 220" has a first set of Bragg gratings disposed on a first "bridge on-ramp segment" 225-1 for coupling to the bus waveguide 210. An optical signal with a central wavelength $\lambda_i$ particular to the Bragg gratings 225-1 disposed on the bridge waveguide 220" is guided through the first bridge ramp segment 225-1 to be reflected into the wavelength selective bridge waveguide 220". The remainder optical signal of the wavelengths $\lambda_1, \lambda_2, \ldots, \lambda_{i-1}, \lambda_{i+1}, \ldots, \lambda_N$ is not affected and continues to transmit over the waveguide 210. The Bragg gratings 225-1 have a specific pitch for reflecting the optical signal of the selected wavelength $\lambda_i$ into the wavelength selective bridge waveguide 220". The wavelength selective bridge waveguide 220" further has a bridge off-ramp segment 225-2" coupled to an outbound waveguide 230" through a coupler 240. The bridge off-ramp segment 225-2" is disposed at a distance from the bridge on-ramp segment 225-1. The bridge waveguide 220 can be an optical fiber, waveguide or other optical transmission medium connected between the bridge on-ramp segment 225-1 and the bridge off-ramp segment 225-2".

FIG. 4A shows structure of an "L" type switch. A wavelength selective bridge waveguide 320 is coupled between a bus waveguide 310 and an intersecting waveguide 330. A multiplexed optical signal is transmitted in a bus waveguide 310 over N multiplexed wavelengths $\lambda_1, \lambda_2, \lambda_3, \ldots, \lambda_N$, where N is a positive integer. The wavelength selective bridge waveguide 320 has a first set of Bragg gratings disposed on a first "bridge on-ramp segment" 325-1 for coupling to the bus waveguide 310. An optical signal with a central wavelength $\lambda_i$ particular to the Bragg gratings 325 disposed on the bridge waveguide 320 is guided through the first bridge ramp segment 325-1 to be reflected into the wavelength selective bridge waveguide 320. The remainder optical signal of the wavelengths $\lambda_1, \lambda_2, \ldots, \lambda_{i-1}, \lambda_{i+1}, \ldots, \lambda_N$ is not affected and continues to transmit over the waveguide 310. The Bragg gratings 325 have a specific pitch for reflecting the optical signal of the selected wavelength $\lambda_i$ into the wavelength selective bridge waveguide 320. The wavelength selective bridge waveguide 320 further has a second set of Bragg gratings 325 as a bridge off-ramp segment 325-2 coupled to an outbound waveguide 330. The bridge off-ramp segment 325-2 is disposed at a distance from the bridge on-ramp segment 325-1. The bridge waveguide 320 can be an optical fiber, waveguide or other optical transmission medium connected between the bridge on-ramp segment and the bridge off-ramp segment 325-2.

FIG. 4B shows another structure of "L" type switches. This structure is similar to that shown in FIG. 4A with the bus waveguide 310 disposed in a vertical direction and an intersecting outbound waveguide 330 disposed along a horizontal direction For simplicity of illustrations FIGS. 5 to 12 show only four wavelengths $\lambda_1, \lambda_2, \lambda_3, \lambda_4$, instead of generalized N wavelengths $\lambda_1, \lambda_2, \lambda_3, \ldots, \lambda_N$.

FIG. 5 shows a drop-before-add optical routing and switching system 800 of this invention. The drop-before-add optical routing and switching system includes an input waveguide designated as waveguide WG(0) for receiving a multiplexed optical signal comprising optical signals transmitted over a plurality of wavelength channels $\lambda_1, \lambda_2, \lambda_3, \lambda_4$, wherein the input waveguide extending over a first horizontal direction. As stated above, the wavelength channels can be $\lambda_1, \lambda_2, \lambda_3, \ldots, \lambda_N$, where N is a positive integer. The routing and switching system further includes a plurality of second direction waveguides WG'(j), j=1, 2, 3, . . . N, extending over a second direction substantially perpendicular to the first direction and intersecting at N intersections with the input waveguide. The optical routing and switching system further includes a plurality of wavelength selective grating switching means SW(j) where j=1, 2, 3, . . . , N, each disposed on one of the N intersections. The wavelength selective grating switching means is employed for selectively transmitting an optical signal of wavelength $\lambda j$ into a waveguide WG'(j) for transmitting to a switching matrix, designated as SWMX, for transmitting the optical signals thereto, and to transmit a dropped optical signal through the input waveguide WG(0). The dropped optical signal consisting of optical signals of wavelengths not selected by the WG'(j) for configuring a drop-before-add optical routing and switching system. By turning switches SW(1), SW(2), and SW(4) on, as illustrated in the case of FIG. 5, $\lambda_1, \lambda_2$, and $\lambda_4$ are selectively transmitting into switching matrix SWMX while $\lambda_3$ is passing along waveguide WG(0) towards the drop end.

FIG. 6 shows a drop-before-add optical routing and switching system 810 of this invention. The drop-before-add optical routing and switching system is similar to that shown in FIG. 5. The input waveguide WG(0) further includes an extension waveguide extending over the first direction parallel to WG(0) designated as WG"(0) for intersecting at N extension-intersections with the plurality of second direction waveguides WG'(j), j=1, 2, 3, . . . , N. The switching and routing system 810 further includes a second set of wavelength selective grating switching means SW'(j), where j=1, 2, 3, . . . , N, each disposed on one of the N extension-intersections. The second set of wavelength selective grating switching means is implemented for wavelength-selectively transmitting a dropped optical signal of wavelength $\lambda j^d$ into a waveguide WG'($j^d$). The routing and switching system 810 further includes a separate drop-signal waveguide WGD. The drop-signal waveguide WGD further intersects with the waveguide WG'(j) on N intersections. Each of these intersections further has a drop-signal switch SWD(j), j=1, 2, 3, . . . N. The drop-signal switch SWD(j) projects the signals received from the WG'($j^d$) to the drop-signal waveguide WGD for transmitting the dropped optical signal of wavelength $\lambda j^d$ with reduced noise of optical signals not exactly having a central wavelength of $\lambda j^d$. All the residual signals are transmitted to a set of optical signal monitors 815 disposed at an opposite end of the switching matrix and connected to each of the optical waveguides WG'(j), j=1, 2, 3, . . . N. By turning on switches SW(1), SW(2), SW(4), SW'(3), and SWD(3), as illustrated in the case of FIG. 6, $\lambda_1$, $\lambda_2$, $\lambda_4$ are selectively transmitting into switching matrix SWMX while $\lambda_3$ is selectively transmitted along waveguide WG"(0), WG'(3), and WGD towards the drop end.

FIG. 7 shows a drop-before-add optical routing and switching system 820 of this invention. The drop-before-add optical routing and switching system is formed with a basic configuration similar to that shown in FIG. 6 except that the wavelength selective switching means SW(j) j=1, 2, 3, ..., N, are kept on continuously for the purpose of de-multiplexing the multiplexed signals. The optical routing and switching system 820 further includes a dropped-signal waveguide designated as waveguide WG"(0) extending over the first direction for intersecting at N extension-intersections with the plurality of second direction waveguides WG'(j), j=1, 2, 3, ... N. The optical routing and switching system further includes a second set of wavelength selective grating switching means SW"(j) where j=1, 2, 3, ..., N, each disposed on one of the N extension-intersections for wavelength-selectively transmitting a dropped optical signal of wavelength $\lambda j^d$ into a waveguide WG'($j^d$) for transmitting the dropped optical signal of wavelength $\lambda j^d$ with reduced noise of optical signals not exactly having a central wavelength of $\lambda j^d$. The optical signal routing and switching system further includes an add-signal waveguide designated as waveguide WGA extending over the first direction for intersecting at N extension-intersections with the plurality of second direction waveguides WG'(j), j=1, 2, 3, ... N, and the waveguide WGA receiving a set of add optical signals. The system further includes a second set of wavelength selective grating switching means SW' (j) where j=1, 2, 3, ..., N, each disposed on one of the N extension-intersections of the add-signal waveguide for wavelength-selectively transmitting an optical signal of wavelength $^a\lambda j$ into the switching matrix as an add signal. With selected switches turned on as indicated in FIG. 7, $\lambda_1$, $\lambda_2$, $^a\lambda_3$, and $\lambda_4$ are selectively transmitting into switching matrix SWMX, while $\lambda_3$ is selectively transmitting towards the drop end.

FIG. 8 shows a drop-before-add optical routing and switching system 830 of this invention. The drop-before-add optical routing and switching system is formed with a basic configuration similar to that shown in FIG. 7 except that the input waveguide WG(0) further includes an extension waveguide extending over the first direction designated as waveguide WG"(0) for intersecting at N extension-intersections with the plurality of second direction waveguides WG'(j), j=1, 2, 3, ... N. The system 830 further includes a second set of wavelength selective grating switching means SW'(j) where j=1, 2, 3, ..., N, each disposed on one of the N extension-intersections for wavelength-selectively transmitting a dropped optical signal of wavelength $\lambda j^d$ into a waveguide WG'($j^d$) for transmitting the dropped optical signal of wavelength $\lambda j^d$ with reduced noise from optical signals not exactly having a central wavelength of $\lambda j^d$. The dropped optical signals transmitted from the drop-signal waveguide WG'($j^d$) are output through waveguide WGD. An optical signal monitor disposed at an opposite end of the switching matrix is connected to each of the optical waveguides WG'(j), j=1, 2, 3, ... N. The routing and switching system 830 further includes a separate drop-signal waveguide WGD. The drop-signal waveguide WGD further intersects with the waveguide WG'(j) on N intersections. Each of these intersections further has a drop-signal switch SWD(j), j=1, 2, 3, ..., N. The drop-signal switch SWD(j) projects the signal received from the WG'($j^d$) to the drop-signal waveguide WGD for transmitting the dropped optical signal of wavelength $\lambda j^d$ to a dropped optical signal monitor (not shown). All the residual signals are transmitted to a set of optical signal monitors disposed at an opposite end of the switching matrix and connected to each of the optical waveguides WG'(j), j=1, 2, 3, ... N. With selected switches turned on as indicated in FIG. 8, $\lambda_1$, $\lambda_2$, $^a\lambda_3$, and $\lambda_4$ are selectively transmitting into switching matrix SWMX, while $\lambda_3$ is selectively transmitting towards the drop end.

FIG. 9 shows a drop-before-add optical routing and switching system 840 of this invention. The drop-before-add optical routing and switching system is formed with a basic configuration similar to that shown in FIG. 7 except that the system 840 further includes a second input waveguide designated as waveguide WG'(0) for receiving a multiplexed optical signal comprising optical signals transmitted over a plurality of wavelength channels represented by $\lambda 1'$, $\lambda 2'$, $\lambda 3'$, ..., $\lambda N'$, where N' is a positive integer, wherein the input waveguide extending over a first direction. The system 840 further includes a plurality of additional second direction waveguides WG'(j'), j=1', 2', 3', ... N', extending over a second direction substantially perpendicular to the first direction and intersecting at additional N' intersections with each of the input waveguide. The system 840 further includes a plurality of wavelength selective grating switching means SW(j) where j=1, 2, 3, ..., N, and SW(j'), j'=1, 2, 3, ..., N' each disposed on one of the N and N' intersections for selectively transmitting an optical signal of wavelength $\lambda j$ and $\lambda j'$ into a waveguide WG'(j) and WG'(j') for transmitting to a switching matrix for adding optical signals therefrom, and for transmitting a dropped optical signal towards the drop end for configuring a drop-before-add optical routing and switching system. Similar to FIG. 6, with selected switches turned on as indicated in FIG. 9, $\lambda 1$, $\lambda 2$, $^a\lambda 3$, $\lambda 4$, and $\lambda 1'$, $\lambda 2'$, $\lambda 3'$, $^a\lambda 4'$ are selectively transmitting into switching matrix SWMX while $\lambda 3$ and $\lambda 4'$ are selectively transmitted towards the drop end.

FIG. 10 shows a drop-before-add optical routing and switching system 850 of this invention. The drop-before-add optical routing and switching system is formed with a basic configuration similar to that shown in FIG. 9 except that in the system 850, the first and the second input waveguides WG(0) and WG'(0) each include a waveguide extension for each of the input waveguides.

FIG. 11 shows a drop-before-add optical routing and switching system 860 of this invention. The drop-before-add optical routing and switching system is formed with a basic configuration similar to that shown in FIG. 9 except that in the system 860, the first and the second input waveguides WG(0) and WG'(0) are merged as a single waveguide WGD' for transmitting the merged dropped signals.

FIG. 12 shows a drop-before-add optical routing and switching system 870 of this invention. The drop-before-add optical routing and switching system is formed with a basic configuration similar to that shown in FIG. 10 except that in the system 870, the first and the second input waveguides WG(0) and WG'(0) are configured horizontally spread out from each other for connecting to a switching matrix SWMX extended over a horizontal direction. The horizontally spread out configuration has an advantage of savings in the manufacturing process by forming two sets of waveguides horizontally. The configuration further achieves savings in space by aligning two sets of side-by-side waveguides in parallel and merging the drop signals in the center.

Although the present invention has been described in terms of the presently preferred embodiment, it is to be understood that such disclosure is not to be interpreted as limiting. Various alternations and modifications will no doubt become apparent to those skilled in the art after reading the above disclosure. Accordingly, it is intended that the appended claims be interpreted as covering all alternations and modifications as fall within the true spirit and scope of the invention.

We claim:

1. A drop-before-add optical routing and switching system comprising:

an input waveguide for carrying a multiplexed optical signal including over a plurality of wavelength channels represented by $\lambda_1, \lambda_2, \lambda_3, \ldots, \lambda_{N-1}$ and $\lambda_N$, wherein said input waveguide extends over a first direction;

a plurality of second direction waveguides extending over a second direction and intersecting at N intersections with said input waveguide; and a plurality of wavelength selective grating switches disposed on said N intersections for selectively transmitting an optical signal of a selected wavelength into an associated one of said second direction waveguides for transmitting to a switching matrix for adding optical signals therefrom, said plurality of wavelength selective grating switches being movable to engage in an on state and disengage in an off state;

further wherein said input waveguide carries a dropped optical signal consisting of optical signals of wavelengths not selected by said grating switches, further wherein the said first direction waveguides and second direction waveguides are formed from the same material.

2. The drop-before-add optical routing and switching system of claim 1 wherein:

said input waveguide further includes an extension waveguide extending from said input waveguide and intersecting at N extension-intersections with said plurality of second direction waveguides;

a second set of wavelength selective grating switches disposed on said N extension-intersections for wavelength-selectively transmitting a dropped optical signal of a selected wavelength into an associated waveguide.

3. The drop-before-add optical routing and switching system of claim 2 further comprising:

an add-signal waveguide intersecting at N intersections with said plurality of second direction waveguides, said add-signal waveguide carrying an add optical signal; and a second set of wavelength selective grating switches each disposed on one of said N intersections of said add-signal waveguide for wavelength-selectively transmitting an optical signal of a selected wavelength into said switching matrix as an add signal.

4. The drop-before-add optical routing and switching system of claim 1 further comprising:

a dropped-signal waveguide for intersecting at N intersections with said plurality of second direction waveguides; and a second set of wavelength selective grating switches each disposed on one of said N intersections for wavelength-selectively transmitting a dropped optical signal of a selected wavelength into an associated waveguide.

5. The drop-before-add optical routing and switching system of claim 4 further comprising:

an add-signal waveguide extending over said first direction for intersecting at N intersections with said plurality of second direction waveguides, said add-signal waveguide carrying an add optical signal; and a second set of wavelength selective grating switches each disposed on one of said N intersections of said add-signal waveguide for wavelength-selectively transmitting an optical signal of a selected wavelength into said switching matrix as an add signal.

6. The drop-before-add optical routing and switching system of claim 1 further comprising:

an add-signal waveguide intersecting at N intersections with said plurality of second direction waveguides, said add-signal waveguide carrying an add optical signal; and a second set of wavelength selective grating switches each disposed on one of said N intersections of said add-signal waveguide for wavelength-selectively transmitting an optical signal of a selected wavelength into said switching matrix as an add signal.

7. The drop-before-add optical routing and switching system of claim 1 further comprising:

a residual input-signal optical port disposed on said input waveguide for connecting and transmitting a residual input optical signal to an optical device.

8. The drop-before-add optical routing and switching system of claim 1 wherein:

each of said plurality of wavelength selective grating switches further comprising Bragg gratings provided for wavelength selectively transmitting an optical signal of a central wavelength particular to said Bragg gratings.

9. The drop-before-add optical routing and switching system of claim 1 wherein:

each of said plurality of wavelength selective grating switches further comprise a coupling waveguide having a first set of Bragg gratings coupled to said input waveguide and a second set of Bragg gratings coupled to said one of said second direction waveguides; and said first set of Bragg gratings for wavelength selectively transmitting an optical signal of a central wavelength particular to said first set of Bragg gratings from said input waveguide to said coupling waveguide and said second set of Bragg gratings for transmitting said optical signal of a central length particular to said second set of Bragg gratings from said coupling waveguide to an intersecting waveguide.

10. The drop-before-add optical routing and switching system of claim 1 further comprising:

a second input waveguide for receiving a second multiplexed optical signal comprising a plurality of wavelength channels $\lambda_1', \lambda_2', \lambda_3', \ldots, \lambda_{N-1}'$ and $\lambda_N'$;

a plurality of additional second direction waveguides intersecting at additional N intersections with each of said input waveguide and said second input waveguide; and a second set of wavelength selective grating switches each disposed on one of said N intersections for selectively transmitting an optical signal of a selected wavelength into an associated one of said second direction waveguides for transmitting to a switching matrix for adding optical signals therefrom, and for transmitting a dropped optical signal through said input waveguide and said second input waveguide.

11. The drop-before-add optical routing and switching system of claim 10 wherein:

said input waveguide and said second input waveguide each having an output end for merging into a merged drop output line.

12. A drop-before-add optical routing and switching system comprising:
   an input waveguide carrying a multiplexed optical signal comprising a plurality of wavelength channels;
   a plurality of wavelength selective grating switches disposed on said input waveguide for selectively transmitting an optical signal of a selected wavelength to a switching matrix whereby optical signals of wavelengths not transmitted by said wavelength selective grating switches are dropped, said plurality of wavelength selective grating switches being movable to engage in an on state and disengage in an off state; and
   each of said wavelength selective grating switches further comprising a Bragg grating for wavelength selectively transmitting an optical signal of a central wavelength particular to said Bragg gratings from said input waveguide to an intersecting waveguide.

13. The drop-before-add optical routing and switching system of claim 12 wherein comprising:
   each of said wavelength selective grating switches further comprise a set of wavelength-specific Bragg gratings surrounded by a refractive-index adjustable medium for selectively switching off and concealing said Bragg grating by adjusting a refractive index of said refraction-index adjustable medium.

14. The drop-before-add optical routing and switching system of claim 12 wherein:
   each of said wavelength selective grating switches further comprise a movable Bragg grating provided for wavelength selectively transmitting an optical signal of a central wavelength particular to said Bragg grating from said input waveguide to said intersecting waveguide whereby said wavelength selective grating switch is on/off switchable.

15. A drop-before-add switch comprising:
   an input waveguide carrying an optical signal comprised of a plurality of wavelengths;
   a plurality of secondary waveguides intersecting with said input waveguide; and
   a plurality of wavelength selective grating switches disposed at the intersection of said plurality of secondary waveguides and said input waveguide, said grating switches selectively operable to couple an associated predetermined wavelength from said plurality of wavelengths from said input waveguide to an associated one of said plurality of secondary waveguides, said plurality of wavelength selective grating switches being movable to engage in an on state and disengage in an off state,
   further wherein the said input waveguide and secondary waveguides are formed from the same material.

16. The switch of claim 15 wherein said grating switches include a Bragg grating.

17. The switch of claim 15 wherein said secondary waveguides are input into a switching matrix.

18. The switch of claim 15 further including:
   an add waveguide that intersects at least one of said plurality of secondary waveguides at a position subsequent to the intersection of said input waveguide and said secondary waveguides, said add waveguide carrying an add optical signal comprised of a plurality of wavelengths; and
   an add grating switch located at the intersection of said add waveguide and said at least one of said plurality of secondary waveguides, said add grating switch operable to selectively couple one of said plurality of wavelengths in said add optical signal to said at least one of said plurality of secondary waveguides.

19. The switch of claim 15 wherein said input waveguide further includes an extension waveguide that further intersects said plurality of secondary waveguides a second time at second intersections, further including second intersection grating switches located at said second intersections.

* * * * *